US008119649B2

(12) United States Patent
Donato et al.

(10) Patent No.: US 8,119,649 B2
(45) Date of Patent: Feb. 21, 2012

(54) USE OF C-SRC INHIBITORS ALONE OR IN COMBINATION WITH STI571 FOR THE TREATMENT OF LEUKAEMIA

(75) Inventors: Nicholas J Donato, Sugar Land, TX (US); Doriano Fabbro, Arlesheim (CH); Paul W Manley, Arlesheim (CH); Jurgen Mestan, Denzlingen (DE); Markus Warmuth, San Marcos, CA (US); Michael Hallek, Cologne (DE); Moshe Talpaz, Houston, TX (US); Ji Wu, Houston, TX (US)

(73) Assignees: Novartis AG, Basel (CH); GSF-International Research Institute for Environment and Health, Oberschleissheim (DE); Board of Regents, The University of Texas system, Austin, TX (US)

(*) Notice: Subject to any disclaimer, the term of this patent is extended or adjusted under 35 U.S.C. 154(b) by 0 days.

(21) Appl. No.: 12/466,186

(22) Filed: May 14, 2009

(65) Prior Publication Data
US 2009/0227608 A1 Sep. 10, 2009

Related U.S. Application Data

(63) Continuation of application No. 11/679,904, filed on Feb. 28, 2007, now abandoned, which is a continuation of application No. 10/485,803, filed as application No. PCT/EP02/08941 on Aug. 9, 2002, now abandoned.

(60) Provisional application No. 60/311,690, filed on Aug. 10, 2001.

(51) Int. Cl.
*A61K 31/519* (2006.01)
(52) U.S. Cl. .................................................. 514/265.1
(58) Field of Classification Search ........................ None
See application file for complete search history.

(56) References Cited

U.S. PATENT DOCUMENTS

| 6,100,254 | A | 8/2000 | Budde et al. ............. 514/221 |
| 2004/0054186 | A1 | 3/2004 | Das et al. ............ 546/268.1 |
| 2005/0215795 | A1 | 9/2005 | Chen et al. ............ 548/190 |

FOREIGN PATENT DOCUMENTS

| CH | 96/10028 | | 4/1996 |
| WO | 96 10028 | | 4/1996 |
| WO | WO 96/10028 | * | 4/1996 |
| WO | WO 97/07131 | | 2/1997 |
| WO | WO 97/08193 | | 3/1997 |
| WO | 97 16452 | | 5/1997 |
| WO | WO 97/28161 | | 8/1997 |
| WO | WO 97/32879 | | 9/1997 |
| WO | WO 97/49706 | | 12/1997 |
| WO | WO 99/03854 | | 1/1999 |
| WO | 00/62778 | | 10/2000 |
| WO | 2004/085388 | | 10/2004 |
| WO | 2005/077945 | | 8/2005 |

OTHER PUBLICATIONS

Dorsey, Jay F., et al., "The Pyrido [2,3-d]pyrimidine Derivative PD180970 Inhibits p210Bcr-Abl Tyrosine Kinase and Induces Apoptosis of K562 Leukemic Cells," Cancer Research, vol. 60, pp. 3127-3131 (2000).*
Buchdunger, Elisabeth, et al, "Bcr-Abl Inhibition As a Modality of CML Therapeutics," Biochimica et Biophysica Act, vol. 1551, pp. M11-M18 (2001).*
Kneissel et al. Calcified Tissue International, 1999, vol. 64, Supplement 1, p. S75 (Abstract attached).*
Gorre et al. Science, Aug. 3, 2001, vol. 293, pp. 876-880.*
Plattner et al. Genes and Development, 1999, vol. 13, pp. 2400-2411.*
Danhauser-Riedl et al. Cancer Res., 1996, vol. 56, pp. 3589-3596.*
Marley S. B. et al., "The tyrosine kinase inhibitor STI571, like interferon-alpha, preferentially reduces the capacity for amplification of granullocyte-macrophase progenitors from patients with chronic myeloid leukemia," Experimental Hematology, New York, NY, vol. 28, pp. 551-557 (2000).
Drummond M.W. et al., "Tyrosine kinase inhibitors in the reatment of chronic myeloid leukemia: so far so good?," Blood Reviews, Edinburgh, GB, vol. 15(2), pp. 85-95 (2001).
Drummond M.W. et al., "Targeting the BCR-ABL tyrosine kinase in chronic myeloid leukemia87 1," New England Journal of Medicine, vol. 344(14), pp. 1084-1086 (2001).
Schindler et al., "Crystal Structure of Hck in Complex with a Src Family-selective Tyrosine Kinase Inhibitor", Mol Cell, vol. 3, pp. 639-648 (1999).

(Continued)

*Primary Examiner* — James D Anderson
(74) *Attorney, Agent, or Firm* — George Dohmann

(57) ABSTRACT

The invention relates to a combination which comprises (a) at least one compound decreasing the c-Src activity and (b) N-{5-[4-(4-methyl-piperazino-methyl)-benzoylamido]-2-methylphenyl}-4-(3-pyridyl)-2-pyrimidine-amine or the monomethanesulfonate salt thereof; to pharmaceutical compositions comprising said combinations; and to a method of treating a warm-blooded animal having leukaemia, especially chronic myelogenous leukaemia, comprising administering to the animal at least one compound inhibiting the activity of a member of the Src kinase family, the Btk kinase family, the Tec kinase family or a Raf kinase inhibitor, in particular inhibiting the c-Src protein tyrosine kinase activity or inhibiting simultaneously the c-Src protein tyrosine kinase activity and the Bcr-Abl tyrosine kinase activity, alone or in combination with a Bcr-Abl inhibitor, in particular N-{5-[4-(4-methyl-piperazino-methyl)-benzoylamido]-2-methylphenyl}-4-(3-pyridyl)-2-pyrimidine-amine.

6 Claims, No Drawings

OTHER PUBLICATIONS

Warmuth et al., Genetic Analysis of the ATP Binding Sites of Hck and Abl Kinases REveal Distinct and Overlapping Determinants for the Specificity of the Tyrosine Kinase Inhibitors PP1 and STI571, Medical Clinic III, University of Munich (D), Abstract No. ONC-00-203.

Warmuth et al., "Dual-specific Src and Abl Kinase Inhibitors, PP1 and CGP76030, Inhibit Growth and Survival of Cells Expressing Imatinib Mesylate-resistant Bcr-Abl Kinases", Blood, vol. 101, No. 2, pp. 664-672 (2003).

Druker B. et al., "Lessons learned from the development of an ABL tyrosine kinase inhibitor for chronic myelogenous leukemia," Journal of Clinical Investigation, vol. 105(1), pp. 3-7 (2000).

Amoui M. et al., "SRC family-selective tyrosine kinase inhibitor, PP1, inhibits both Fcepsilonri- and thy-1-mediated activation of rat basophilic leukemia cells," European Journal of immunology, vol. 27(8), pp. 1881-1886 (1997).

Dorsey J.F. et al., "Pyrido1,3-dpyrimidine derivative PD180970 inhibits P210BCR-ABL tyrosine kinase and induces apoptosis of K562 leukemic cells," Cancer Research, American Associationf or Cancer Research. vol. 60, pp. 3127-3131 (2000).

Hamby J.M. et al., "Structure-activity relationships for a novel series of pyridoä2,3-düpyrimidine tyrosine kinase inhibitors," Journal of Medicinal Chemistry, vol. 40(15), p. 2296-2303 (1997).

Gamse R. et al., "NVP-AAK980, a novel 6-phenylamino-2-alkylamino-purine derivative, potently inhibits the tyrosine kinase SRC and bone resorption," Journal of Bone and Mineral Research, vol. 14, pp. S487 (1999).

Klutchko S.R. et al., "2-substituted aminopyridoä2,3-düpyrimidin-7(8H)-ones. Structure-activity relationships against selected tyrosine kinases and in vitro and in vivo anticancer activity," Journal of Medicinal Chemistry, vol. 41(17), pp. 3276-3292 (1998).

Panek R.L. et al., "In vitro pharmacological characterization of PD 166285, a new nanomolar potent and broadly active protein tyrosine kinase inhibitor," Journal of Pharmacology and Experimental Therapeutics, American Society for Pharmacology and, US. vol. 283(3), pp. 1433-1444(1997).

Hanke J.H. et al., "Discovery of a novel, potent, and SRC family-selective tyrosine kinase inhibitor" Journal of Biological Chemistry, vol. 271(2), pp. 695-701 (1996).

Topaly J. et al., "Synergistic activity of the new ABL-specific tyrosine kinase inhibitor STI571 and chemotherapeutic drugs on BCR-abl-positive chronic myelogenous leukemia cells," Leukemia, vol. 15, pp. 342-347 (2001).

Kano Y. et al., "In vitro cytotoxic effects of a tyrosine kinase inhibitor STI571 in combination with commonly used antileukemic agents," Blood, vol. 97(7), pp. 1999-2007 (2001).

Tyler Thiesing J. et al., "Efficacy of STI571, an ABL tyrosine kinase inhibitor, in conjunction with other antileukemic agents against BCR-ABL-positive cells," Blood, vol. 96(9), pp. 3195-3199 (2000).

Bazzoni, Carlesso, Griffin and Hemler, Bcr/Abl Expression Stimulates Integrin Function in Hematopoietic Cell Lines, J Clin Invest, vol. 98, No. 2, pp. 521-528 (1996).

Liu et al., "Structural Basis for Selective Inhibition of Src Family Kinases by PP1", Chem Biol, vol. 6, No. 9, pp. 671-678 (1999).

Missbach, Altmann and Susa, "Tyrosine Kinase Inhibition in Bone Metabolism", Curr Opin Drug Dis Dev, vol. 3, No. 5, pp. 541-548 (2000).

Donato et al., "BCR-ABL independence and LYN kinase overexpression in chronic myelogenous leukemia cells selected for resistance to STI571", Blood, vol. 101, No. 2, pp. 690-698, (2003).

Drug Data Rep. 2004, 26(11), 1075.

Adis R&D Insight database, Dec. 16, 2005.

Idb3 database, Dec. 16, 2005.

IMS Life Cycle, Dec. 16, 2005.

J. Travis, Science, vol. 305, No. 5682, pp. 319-321, (2004).

N.P. Shah et al., "Overiding Imatinib Resistance with a Novel ABL Kinase Inhibitor", Science, vol. 305, pp. 399-401, (2004).

Nature Reviews Drug Discovery, 3(8), 636, (2004).

M.W.N. Deininger e al., "SRCircumventing imatinib resistance", Cancer Cell, vol. 6, No. 2, pp. 108-110, (2004).

Abstract, C. Sawyers et al., blood, Nov. 16, 2004, vol. 104, No. 11, Part 1, pp. 4-A.

Abstract, M. Talpaz et al., Blood, Nov. 16, 2004, vol. 104, No. 11, Part 1, pp. 10A.

Abstract, M. Burgess et al., blood, Nov. 16, 2004, vol. 104, No. 11, Part 1, pp. 160A.

Abstract, N. Shah et al., Blood, Nov. 16, 2004, vol. 104, No. 11, Part 1, pp. 288A.

Yiguo Hu et al., "Requirement of Src kinases Lyn, Hck and Fgr for BCR-ABL1-induced B-lymphoblastic leukemia but not chronic myeloid leukemia", Nature Genetics, vol. 36, No. 5, (2004).

Talpaz M. et al., "Downrequlation of Bcr-abl expression and kinase activity but . . . ", Blood, vol. 96, p. 345a, 2000, Abstract: 1488.

Donato N. et al., "A Dominant role for LYN Kinase in K562 Cells selected for Resistance to STI-571", Blood, p. 3487, 2000, Abstract: 3487.

Buchdunger, Elisabeth, et al., "Bcr-Abl Inhibition as a Modality of CML Therapeutics". Biochimica et Biophysica Act, vol. 1551, pp. M11-M18, (2001).

Haney, Daniel: "Strategy aims to starve rather than poison cancer,", Hannibal Courier-Post, www.hannibal.net/cgi-bin/printtime.pl. (pp. 1-5)(1999).

Kitanka, et al., "Antisense SRC Expression Inhibits Proliferation and Erythropoietin-Induced Erythroid Differentiation of K562 Human Leukemia Cells", Biochemical and Biophysical Research communications, V. 201:3, 1994, pp. 1534-1540.

* cited by examiner

USE OF C-SRC INHIBITORS ALONE OR IN COMBINATION WITH STI571 FOR THE TREATMENT OF LEUKAEMIA

This is a continuation of application Ser. No. 11/679,901 filed on Feb. 28, 2007, which is a continuation of application Ser. No. 10/485,803 filed on Jul. 29, 2004, which is a 371 of PCT/EP02/08941 filed on Aug. 9, 2002 which claims the benefit of U.S. Provisional application No. 60/311,690 filed on Aug. 10, 2001, the entire disclosures of which are hereby incorporated by reference.

The invention relates to a method of treating a warm-blooded animal, especially a human, having leukaemia comprising administering to the animal at least one compound inhibiting the c-Src protein tyrosine kinase activity, especially those compounds mentioned herein, in a quantity which is effective against leukaemia; to a method of treating a warm-blooded animal, especially a human, having leukaemia comprising administering to the animal (a) at least one compound decreasing the c-Src activity and (b) N-{5-[4-(4-methyl-piperazino-meth)-benzoylamido]-2-methylpheny}-4-(3-pyridyl)-2-pyrimidine-amine (STI571) in a quantity which is jointly therapeutically effective against leukaemia; a combination which comprises (a) at least one compound decreasing the c-Src activity and (b) STI571 or the monomethanesulfonate salt thereof and optionally at least one pharmaceutically acceptable carrier for simultaneous, separate or sequential use; a pharmaceutical composition comprising such a combination; the use of a compound inhibiting the c-Src protein tyrosine kinase activity or the use of the combination of (a) and (b) for the preparation of a medicament for the delay of progression or treatment of leukaemia; and to a commercial package or product comprising such a combination of (a) and (b) or at least one compound inhibiting the c-Src protein tyrosine kinase activity together with instructions for use thereof in the treatment of leukaemia.

Protein tyrosine kinases catalyze the phosphorylation of specific tyrosine residues. One member of this class of enzymes is the c-Src protein tyrosine kinase. Surprisingly, it has now been found that compounds inhibiting the c-Src protein tyrosine kinase activity, especially the compounds described hereinafter, are effective against leukaemia. Furthermore, it was surprisingly found that the effect in treating leukaemia of a combination which comprises (a) at least one compound decreasing the c-Src activity and (b) STI571 or the monomethane-sulfonate salt thereof is greater than the effects that can be achieved with either type of combination partner alone, i.e. greater than the effects of a monotherapy using only one of the combination partners (a) and (b) as defined herein.

Hence, in a first embodiment, the present invention relates to a method of treating a warm-blooded animal having leukaemia comprising administering to the animal at least one compound inhibiting the c-Src protein tyrosine kinase activity in a quantity which is therapeutically effective against leukaemia, in which method said compounds can also be present in the form of their pharmaceutically acceptable salts.

In a second embodiment, the present invention relates to a method of treating a warm-blooded animal having leukaemia comprising administering to the animal (a) at least one compound decreasing the c-Src activity and (b) STI571 in a quantity which is jointly therapeutically effective against leukaemia.

Furthermore, the present invention relates to a combination which comprises (a) at least one compound decreasing the c-Src activity and (b) STI571, wherein the active ingredients are present in each case in free form or in the form of a pharmaceutically acceptable salt, and optionally at least one pharmaceutically acceptable carrier; for simultaneous, separate or sequential use.

In a broader sense, the present invention relates to a method of treating a warm-blooded animal having leukaemia, in particular comprising administering to the animal at least one compound inhibiting the activity of a member of the Src kinase family, in particular src, yes, hck, fyn, lyn, lck, blk, fgr or Yrk, the activity of a member of the Btk or Tec kinase family or a Raf kinase inhibitor, e.g. BAY 43-9006, in a quantity which is therapeutically effective against leukaemia alone or in combination with a Bcr-Abl inhibitor, in particular STI571.

The term leukemia as used herein includes, but is not limited to, chronic myelogenous leukaemia (CML) and acute lymphocyte leukaemia (ALL), especially Philadelphia-chromosome positive acute lymphocyte leukaemia (Ph+ ALL). Preferably, the variant of leukaemia to be treated by the methods disclosed herein is CML.

The term "method of treatment" as used herein includes a treatment effecting the delay of progression of leukemia. The term "delay of progression" as used herein means in particular the administration of a medicament to patients being in a pre-stage or in an early phase of leukaemia, in which patients, for example, a pre-form or an early form of leukaemia is diagnosed or which patients are in a condition, e.g. a condition resulting from an accident, under which it is likely that a corresponding disease will develop.

The term "compounds inhibiting the c-Src protein tyrosine kinase activity" as used herein means such compounds having an $IC_{50}$ in the range of 1 to 3000 nM, preferably in the range of 1 to 500 nM, in the proliferation test using bcr-Abl transfected 32D cells described hereinafter. The term includes, but is not limited to, compounds belonging to the structure classes of pyrrolopyrimidines, especially pyrrolo[2,3-d]pyrimidines, purines, pyrazopyrimidines, especially pyrazo[3,4-d]pyrimidines, pyrazopyrimidines, especially pyrazo[3,4-d]pyrimidines and pyridopyrimidines, especially pyrido[2,3-d]pyrimidines. Preferably, the term relates to those compounds disclosed in WO 96/10028, WO 97/28161, WO97/32879 and WO97/49706 and, more preferably, to the single compounds of formulae I to VIII, most preferably to the compound of formula I and V, in particular the compound of formula I.

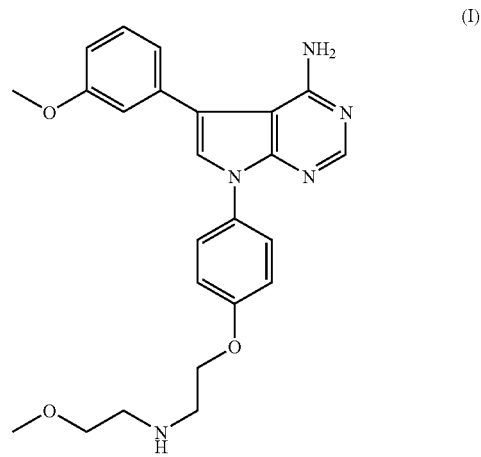

(I)

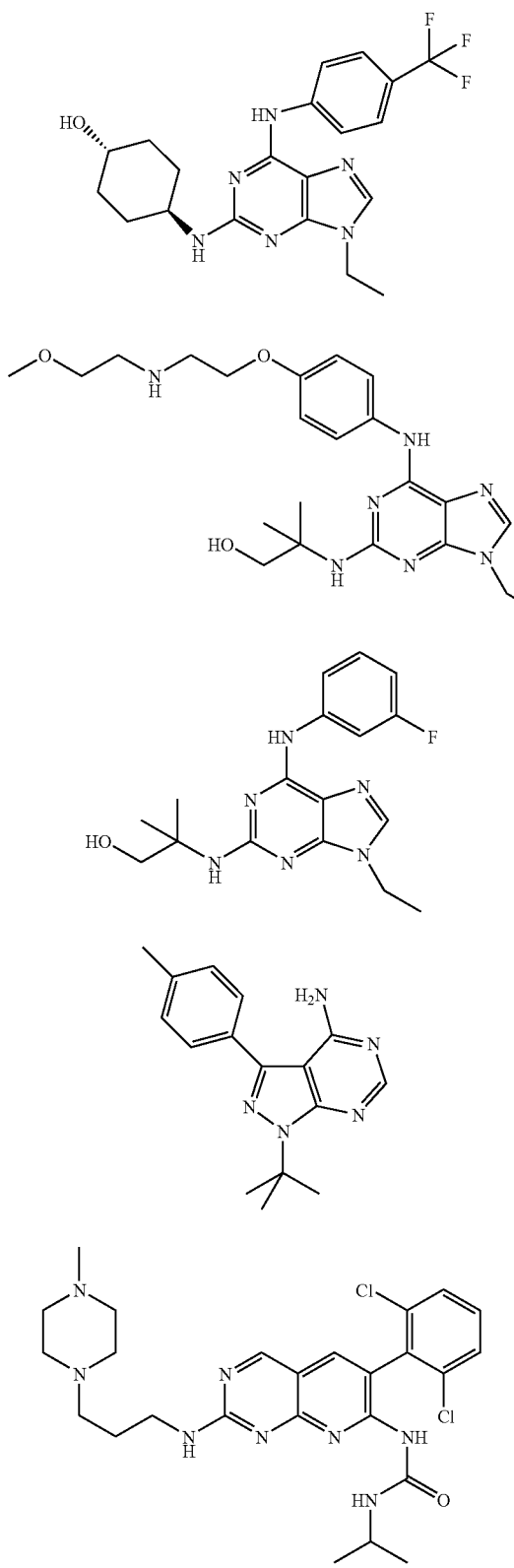
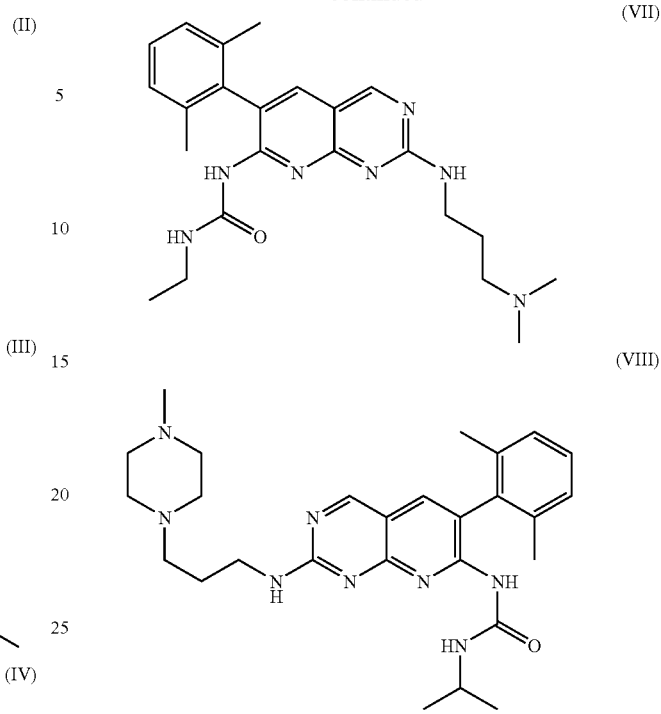

The compounds which are generically and specifically disclosed in WO 96/10028, WO 97/28161, WO97/32879 and WO97/49706, in each case in particular in the compound claims and the final products of the working examples, are hereby incorporated into the present application by reference to these publications. The compounds can be prepared and administered as described in the cited documents, respectively. The compound of formula I can be prepared and formulated as described in WO 96/10028. The compound of formula II and its preparation is disclosed in Example 111c3 of WO 97/16452. The compound of formula IV can be prepared in analogy thereof. Both latter compounds can be formulated as described in WO 97/16452. The compound of formula III is discussed by R. Gamse et al. in J. Bone Miner. Res. 14 (Suppl. 1), 1999, S487. The compound of formula V is also known as PP1. The preparation of PP1 is described by T. Schindler, F. Sicheri et al in Molecular Cell, 1999 (3), 639, 647. The compounds of formula VI, VII and VIII are described in the following documents and the literature cited therein: J. M. Hamby et al, J. Med. Chem. 40, 1997, 2296-2303; R. L. Panek et al, J. Pharmacol. Exp. Ther. 283, 1997, 1433-1444; and S. R. Klutchko et al, J. Med. Chem. 41, 1998, 3276-3292.

STI571 can be prepared and administered as described in WO 99/03854, especially the monomesylate salt of STI571 can be formulated as described in Examples 4 and 6 of WO 99/03854. STI571 can also be administered as marketed under the trademark GLIVEC™ or GLEEVEC™.

The term "compounds decreasing the c-Src activity" as used herein includes, but is not limited to, compounds inhibiting the c-Src protein tyrosine kinase activity as defined above and to SH2 interaction inhibitors such as those disclosed in WO97/07131 and WO97/08193. Preferably, in the present invention compounds decreasing the c-Src activity are SH2 interaction inhibitors or, more preferably, compounds inhibiting the c-Src protein tyrosine kinase activity as defined above.

It will be understood that references to the pharmacologically active compounds mentioned herein are meant to also include the pharmaceutically acceptable salts. If compounds inhibiting the c-Src protein tyrosine kinase activity or a combination partner (a) or (b) have, for example, at least one basic center, they can form acid addition salts. The combination partners (a) and (b) having an acid group (for example COOH) can also form salts with bases. The pharmacologically active compounds mentioned herein may also be used in form of a hydrate or include other solvents used for crystallization. STI571, i.e. the combination partner (b), is preferably used in the present invention in the form of its monomesylate salt.

Additionally, the present invention relates to a method of treating a warm-blooded animal having leukaemia comprising administering to the animal at least one compound inhibiting the c-Src protein tyrosine kinase activity and the Bcr-Abl tyrosine kinase activity, in a quantity which is therapeutically effective against leukaemia, in which method said compounds can also be present in the form of their pharmaceutically acceptable salts. Preferably, such compound is a compound of formula V.

The utility of the compounds inhibiting the c-Src protein tyrosine kinase activity for the treatment of leukemia can be demonstrated, e.g., in the proliferation test using bcr-Abl transfected 32D cells as follows:

Bcr-Abl-transfected 32D cells (32D pGD p210 Bcr-Abl; Bazoni, G.; et al. J. Clin. Invest. (1996), 98(2), 521-528) are cultured in RPMI 1640 (BioConcept, Allschwil, Switzerland; cat. No.: 1-41F01), 10% fetal calf serum, 2 mM glutamine. 10000 cells in 50 µL per well are seeded into flat bottom 96 well tissue culture plates. Complete medium alone (for controls) or serial threefold dilutions of compounds are added in triplicates to a final volume of 100 µL and the cells are incubated at 37° C., 5% $CO_2$ for 65 to 72 h. The cell proliferation reagent WST-1 (Roche Diagnostics GmbH; cat.no.: 1 664 807) is added at 10 µL per well followed by 2 h incubation at 37° C. Colour development, depending on the amount of living cells, is measured at 440 nm. The effect for each compound is calculated as percent inhibition of the value ($OD_{440}$) obtained for the control cells (100%) and plotted against the compound concentrations. The $IC_{50}$s are calculated from the dose response curves by graphic extrapolation.

Compounds inhibiting the growth of 32D-Bcr-Abl cells can be further tested on IL-3 dependent 32D wt cells to prove the specificity of the compounds for the bcr-Abl kinase and to exclude compound toxicity.

A combination which comprises (a) at least one compound decreasing the c-Src activity and (b) STI571, wherein the active ingredients are present in each case in free form or in the form of a pharmaceutically acceptable salt, and optionally at least one pharmaceutically acceptable carrier will be referred to hereinafter as a COMBINATION OF THE INVENTION.

The nature of proliferative diseases like leukemia is multifactorial. Under certain circumstances, drugs with different mechanisms of action may be combined. However, just considering any combination of drugs having different mode of action does not necessarily lead to combinations with advantageous effects.

All the more surprising is the experimental finding that the administration of a COMBINATION OF THE INVENTION, results not only in a beneficial effect, especially a synergistic therapeutic effect, e.g. with regard to slowing down, arresting or reversing the progress of leukaemia or a longer duration of drug response, but also in further surprising beneficial effects, e.g. less side-effects, an improved quality of life and a decreased mortality and morbidity, compared to a monotherapy applying only one of the pharmaceutically active ingredients used in the COMBINATION OF THE INVENTION.

A further benefit is that lower doses of the active ingredients of the COMBINATION OF THE INVENTION can be used, for example, that the dosages need not only often be smaller, but can be also applied less frequently, or can be used in order to diminish the incidence of side-effects. This is in accordance with the desires and requirements of the patients to be treated.

The utility of the COMBINATION OF THE INVENTION for the treatment of leukemia can be demonstrated, e.g., in the proliferation test using bcr-Abl transfected 32D cells as follows:

The proliferation test using bcr-Abl transfected 32D cells with a COMBINATION OF THE INVENTION is carried out as described above with the following changes. Two combination partners are mixed in fixed ratios. Threefold serial dilutions of this mixture or the combination partners alone are added to the cells seeded in 96 well tissue culture plates as described above. The effects on 32D-bcr-Abl cell proliferation of a COMBINATION OF THE INVENTION is evaluated and compared with the effects of the single combination partners using CalcuSyn, a dose-effect analyzer software for single and multiple drugs (distributed by Biosoft, Cambridge).

One particular benefit of the present invention is the fact that the leukaemia that can be treated with a compound inhibiting the c-Src protein tyrosine kinase activity or with the COMBINATION OF THE INVENTION can be such leukaemia which is resistent to monotherapy employing STI571 as sole active agent, e.g. leukaemia of such patients who initially had responded to STI571 and then relapsed. Very especially, compounds inhibiting the c-Src protein tyrosine kinase activity and COMBINATIONS OF THE INVENTION can be used for the treatment of patients in the advanced stage (blast crisis phase) of CML.

The person skilled in the pertinent art is fully enabled to select further relevant test modesl to prove the hereinbefore and hereinafter mentioned beneficial effects on leukaemia of a compound inhibiting the c-Src protein tyrosine kinase activity or of a COMBINATION OF THE INVENTION. The pharmacological activity of a compound inhibiting the c-Src protein tyrosine kinase activity or a COMBINATION OF THE INVENTION may, for example, be demonstrated in a suitable clinical study. Suitable clinical studies are, for example, open label non-randomized, dose escalation studies in patients with advanced leukaemia. Such studies prove in particular the synergism observed with the COMBINATIONS OF THE INVENTION. The beneficial effects on leukaemia can be determined directly through the results of these studies or by changes in the study design which are known as such to a person skilled in the art. For example, the combination partner (b) can be administered with a fixed dose and the dose of the combination partner (a) is escalated until the Maximum Tolerated Dosage is reached. Alternatively, a placebo-controlled, double blind study can be conducted in order to prove the benefits of the COMBINATION OF THE INVENTION mentioned herein.

In one embodiment of the invention, the compound inhibiting the c-Src protein tyrosine kinase activity is selected from pyrrolopyrimidines, especially pyrrolo[2,3-d]pyrimidines, purines, pyrazopyrimidines, especially pyrazo[3,4-d]pyrimidines, pyrazopyrimidines, especially pyrazo[3,4-d]pyrimidines and pyridopyrimidines, especially pyrido[2,3-d]-pyrimidines. Particularly preferred are the compounds of formula I, II, III, IV, V, VI, VII and VIII, especially the compound of formula I and formula V.

Especially preferred is a combination comprising a compound of formula I and STI571 or the pharmaceutically acceptable salts thereof. Furthermore, especially preferred is a combination comprising a compound of formula V and STI571 or the pharmaceutically acceptable salts thereof.

The invention pertains also to the use of at least one compound inhibiting the c-Src protein tyrosine kinase activity or of the COMBINATION OF THE INVENTION for the treatment of leukaemia and for the preparation of a medicament for the treatment of leukaemia.

The COMBINATION OF THE INVENTION can be a combined preparation or a pharmaceutical composition.

The term "a combined preparation", as used herein defines especially a "kit of parts" in the sense that the combination partners (a) and (b) as defined above can be dosed independently or by use of different fixed combinations with distinguished amounts of the combination partners (a) and (b), i.e., simultaneously or at different time points. The parts of the kit of parts can then, e.g., be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the combination partners (a) and (b). The ratio of the total amounts of the combination partner (a) to the combination partner (b) to be administered in the combined preparation can be varied, e.g. in order to cope with the needs of a patient sub-population to be treated or the needs of the single patient which different needs can be due to the particular disease, age, sex, body weight, etc. of the patients. Preferably, there is at least one beneficial effect, e.g., a mutual enhancing of the effect of the combination partners (a) and (b), in particular a synergism, e.g. a more than additive effect, additional advantageous effects, less side effects, a combined therapeutical effect in a non-effective dosage of one or both of the combination partners (a) and (b), and very preferably a strong synergism of the combination partners (a) and (b).

It is one objective of this invention to provide a pharmaceutical composition comprising a quantity, which is jointly therapeutically effective against leukaemia comprising the COMBINATION OF THE INVENTION. In this composition, the combination partners (a) and (b) can be administered together, one after the other or separately in one combined unit dosage form or in two separate unit dosage forms. The unit dosage form may also be a fixed combination.

The pharmaceutical compositions for separate administration of the combination partners (a) and (b) and for the administration in a fixed combination, i.e. a single galenical compositions comprising at least two combination partners (a) and (b), according to the invention can be prepared in a manner known per se and are those suitable for enteral, such as oral or rectal, and parenteral administration to mammals (warm-blooded animals), including man, comprising a therapeutically effective amount of at least one pharmacologically active combination partner alone or in combination with one or more pharmaceutically acceptable carries, especially suitable for enteral or parenteral application.

Novel pharmaceutical composition contain, for example, from about 10% to about 100%, preferably from about 20% to about 60%, of the active ingredients. Pharmaceutical preparations for the combination therapy for enteral or parenteral administration are, for example, those in unit dosage forms, such as sugar-coated tablets, tablets, capsules or suppositories, and furthermore ampoules. If not indicated otherwise, these are prepared in a manner known per se, for example by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can be reached by administration of a plurality of dosage units.

In particular, a therapeutically effective amount of each of the combination partner of the COMBINATION OF THE INVENTION may be administered simultaneously or sequentially and in any order, and the components may be administered separately or as a fixed combination. For example, the method of treatment of leukaemia according to the present invention may comprise (i) administration of the combination partner (a) in free or pharmaceutically acceptable salt form and (ii) administration of a combination partner (b) in free or pharmaceutically acceptable salt form, simultaneously or sequentially in any order, in jointly therapeutically effective amounts, preferably in synergistically effective amounts, e.g. in daily dosages corresponding to the amounts described herein. The individual combination partners of the COMBINATION OF THE INVENTION can be administered separately at different times during the course of therapy or concurrently in divided or single combination forms. Furthermore, the term administering also encompasses the use of a pro-drug of a combination partner that convert in vivo to the combination partner as such. The instant invention is therefore to be understood as embracing all such regimes of simultaneous or alternating treatment and the term "administering" is to be interpreted accordingly.

The effective dosage of each of compounds inhibiting the c-Src protein tyrosine kinase activity and of the combination partners employed in the COMBINATION OF THE INVENTION may vary depending on the particular compound or pharmaceutical composition employed, the mode of administration, the condition being treated, the severity of the condition being treated, Thus, the dosage regimen the COMBINATION OF THE INVENTION is selected in accordance with a variety of factors including the route of administration and the renal and hepatic function of the patient. A physician, clinician or veterinarian of ordinary skill can readily determine and prescribe the effective amount of the single active ingredients required to prevent, counter or arrest the progress of the condition. Optimal precision in achieving concentration of the active ingredients within the range that yields efficacy without toxicity requires a regimen based on the kinetics of the active ingredients' availability to target sites.

N-{5-[4-(4-methyl-piperazino-methyl)-benzoylamido]-2-methylphenyl}-4-(3-pyridyl)-2-pyrimidine-amine monomesylate, is preferably administered to a human in a dosage in the range of about 5 to 850 mg/day, more preferably 25 to 600 mg/day and most preferably 100 to 300 mg/day. Unless stated otherwise herein, the compound is preferably administered from one to four times per day. Compounds inhibiting the c-Src protein tyrosine kinase activity, e.g. the compound of formula I, is preferably administered orally to a human in a dosage in the range of about 100 to 2000 mg/day, more preferably 500 to 1500 mg/day, e.g. 1000 mg/day.

If BAY 43-9006 is employed as a combination partner, it is preferably administered orally at doses of up to 800 mg twice daily.

Moreover, the present invention provides a commercial package comprising as active ingredients COMBINATION

OF THE INVENTION, together with instructions for simultaneous, separate or sequential use thereof in the treatment of leukaemia.

What is claimed is:

1. A combination which comprises (a) a compound of formula I

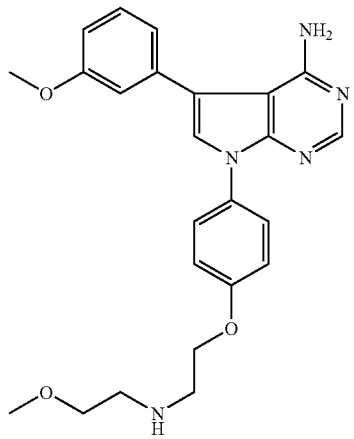

and (b) N-{5-[4-(4-methyl-piperazino-methyl)-benzoylamido]-2-methylphenyl}-4-(3-pyridyl)-2-pyrimidine-amine, wherein each compound is present in free form or in the form of a pharmaceutically acceptable salt, and optionally at least one pharmaceutically acceptable carrier; for simultaneous, or sequential use.

2. The combination according to claim 1 wherein compound (b) is used in the form of its monomethanesulfonate salt.

3. A method of treating leukaemia in a warm-blooded animal comprising administering to said animal an effective amount of N-{5-[4-(4-methyl-piperazino-methyl)-benzoylamido]-2-methylphenyl}-4-(3-pyridyl)-2-pyrimidine-amine in combination with an effective amount of a compound of formula I

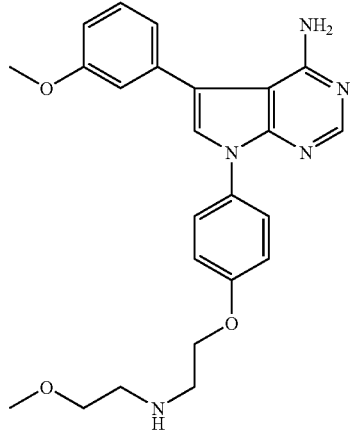

wherein the active ingredients are present in free form or in the form of a pharmaceutically acceptable salt.

4. The method according to claim 3 wherein said leukaemia is resistant to mono-therapy employing N-{5-[4-(4-methyl-piperazino-methyl)-benzoylamido]-2-methylphenyl}-4-(3-pyridyl)-2-pyrimidine-amine as sole active agent.

5. The method according to claim 3 wherein said leukaemia is chronic myelogenous leukaemia.

6. A pharmaceutical composition comprising the combination according to claim 1 and at least one pharmaceutically acceptable carrier.

* * * * *